United States Patent [19]
Baker

[11] Patent Number: 6,119,437
[45] Date of Patent: Sep. 19, 2000

[54] METHOD OF PRODUCING FINGER DRYING MATERIAL USED FOR INSERTION OF CONTACT LENSES

[75] Inventor: Todd Baker, Pacific Palisades, Calif.

[73] Assignee: Palisades Eye Care Company, Pacific Palisades, Calif.

[21] Appl. No.: 09/022,105

[22] Filed: Feb. 11, 1998

[51] Int. Cl.[7] .................................................. B65B 55/02
[52] U.S. Cl. .................................................. 53/425
[58] Field of Search .............................. 34/245, 246, 255, 34/345, 355, 95; 53/425; 602/42, 57

[56] References Cited

U.S. PATENT DOCUMENTS

| | | | |
|---|---|---|---|
| 4,754,595 | 7/1988 | Sanderson | 53/425 |
| 5,478,308 | 12/1995 | Cartmell et al. | 602/57 |
| 5,623,810 | 4/1997 | Dey et al. | 53/425 |
| 5,843,374 | 12/1998 | Sizer et al. | 422/24 |
| 5,868,244 | 2/1999 | Ivanov et al. | 206/63.3 |

OTHER PUBLICATIONS

"Quick Tips for Success with Focus Programmed Replacement Lenses" CIBA Vision Corporation brochure, 1990.

*Primary Examiner*—Stephen Gravini

[57] ABSTRACT

A method for drying the applicating finger of a contact lens wearer with sterile, lint-free, absorbent paper. The applicating finger is used to remove the contact lens from an aqueous solution. The lens is then transferred from the applicating finger, and the applicating finger is dried by contact with the sterile, lint-free, absorbent paper. Thereafter, the lens is returned to the dry applicating finger for insertion of the contact lens onto the eye.

10 Claims, 2 Drawing Sheets

METHOD OF PRODUCING FINGER DRYING MATERIAL USED FOR INSERTION OF CONTACT LENSES

FIELD OF THE INVENTION

This invention relates to the application of contact lenses onto the eye. More specifically, the invention relates to a method and system for drying the fingertip used to apply the lens onto the eye with sterile, lint-free, absorbent paper.

BACKGROUND OF THE INVENTION

Soft contact lenses, by composition, are roughly thirty-five to seventy percent water. Contact lenses are hydrophilic and are stored in aqueous solution, from which the contact lens wearer removes them prior to inserting the lenses onto the eye. In order to insert a contact lens onto the eye, the fingertip (usually the tip of the index finger or middle finger) which applies the lens to the eye must be dry enough so that the lens sits up on the fingertip in a concave fashion. If the fingertip is too wet, the hydrophilic lens flops over or flattens out on the fingertip, making the lens' application to the convex eye surface difficult. Moreover, even if the lens sits up concavely on a wet fingertip, the moisture on the fingertip tends to cling to the moisture of the lens, making the lens transfer from the fingertip to the eye extremely difficult.

Currently contact lens manufacturers recommend that before handling a contact lens, the wearer wash his hands and dry them completely with a lint-free towel. The wearer then removes the lens from storage in the aqueous solution. The wearer removes the lens from the storage solution with his applicating finger, and then transfers the lens to the opposite hand, usually to the thumb and forefinger of the opposite hand. The lens wearer then transfers the lens back to his applicating finger for insertion of the lens onto his eye.

Because the wearer's applicating finger becomes wetted when removing the lens from the aqueous storage solution, the applicating finger must be dried before it can be used to insert the contact lens onto the eye. However, the contact lens wearer is currently not provided, either professionally or commercially, with a material which is adequate for the purpose of drying his contact lens applicating finger.

From the recommendation of contact lens manufacturers, the lens wearer may understand that the material used for drying his lens applicating finger should be lint-free. To prevent introduction of harmful bacteria into the wearer's eye, the material should also be sterile. Of course, the material must also be absorbent in order to dry the applicating finger before it is used to insert the lens onto the eye.

While absorbent, household towels, e.g., bath or hand towels, gather dust and lint. Thus, if such a towel is used to dry the lens wearer's applicating finger, dust and lint are transferred to the contact lens and therefore to the eye. Facial tissues, toilet paper and paper towels are also inadequate because they leave bits of paper pulp on the applicating finger, which is then transferred to the eye. Such small pieces of paper pulp lint severely irritate the eye. Similarly, cotton balls are inadequate because they leave cotton fibers on the applicating finger which are then transferred to the eye.

Wax paper and tissues used for cleaning eye glasses or camera lenses are somewhat lint-free. However, these materials are inadequate because they are not sufficiently absorbent.

SUMMARY OF THE INVENTION

In accordance with one aspect of the invention, lint-free, absorbent paper is cut into small sheets suitably sized for drying fingertips. The paper sheets are packaged in a container. The packaged sheets are sterilized, for example, by gamma radiation.

In another aspect of the invention, the sterile, lint-free, absorbent sheets are provided to a contact lens wearer with instructions to dry his lens applicating finger by contact with one of the sheets prior to inserting a contact lens onto the eye.

In a further aspect of the invention, the lens wearer is instructed to remove the contact lens from an aqueous solution with one of his fingers (the applicating finger). The lens wearer then transfers the lens from his applicating finger to, for example, the thumb and forefinger of his opposite hand. Thereafter, he dries his applicating finger by contact with the sterile, lint-free, absorbent paper sheets. The lens wearer then uses his dry applicating finger to insert the contact lens onto his eye.

DETAILED DESCRIPTION OF THE INVENTION

It has been discovered by the present inventor that towelette paper, after being processed in accordance with the invention, is ideal for drying the fingertip used to apply a contact lens onto the eye. In the preferred embodiment of the invention, the towelette paper used is manufactured by J. Ford Ltd. of Portneuf, Quebec, Canada and sold under identifiers DD18 to DD22. In the most preferred embodiment, DD20 towelette paper is used. Such paper exhibits the necessary lint-free and absorbency characteristics. Other paper of like basis/weight and composition is satisfactory.

As manufactured, DD20 towelette paper is not suitable for use with the invention because it is not sterile enough to be contacted by a fingertip used to insert a contact lens onto the eye. Accordingly, the DD20 towelette paper, which is typically available in twelve foot rolls of 3000 square feet is cut to size, packaged and sterilized.

Illustratively, the paper is cut into a plurality of four inch by four inch square sheets, stacked and placed in a container holding, for example, 100 sheets. A cardboard box is a useful container since it can be printed with source identifying labels and/or instruction to contact lens wearers. To sterilize the sheets, the packaged sheets are subjected to low-level gamma radiation. Subjecting the sheets to such radiation for a period of at least eight hours provides adequate sterilization.

Use of DD18 to DD20 towelette paper for the purpose of the present invention is a marked departure form its prior uses known to the present inventor. Conventionally, such paper is soaked with chemical-based cleaning agents prior to being provided to end users. Even a small amount of such cleaning agents would cause severe irritation and possibly permanent damage to the eye if applied thereto.

Figure 1:
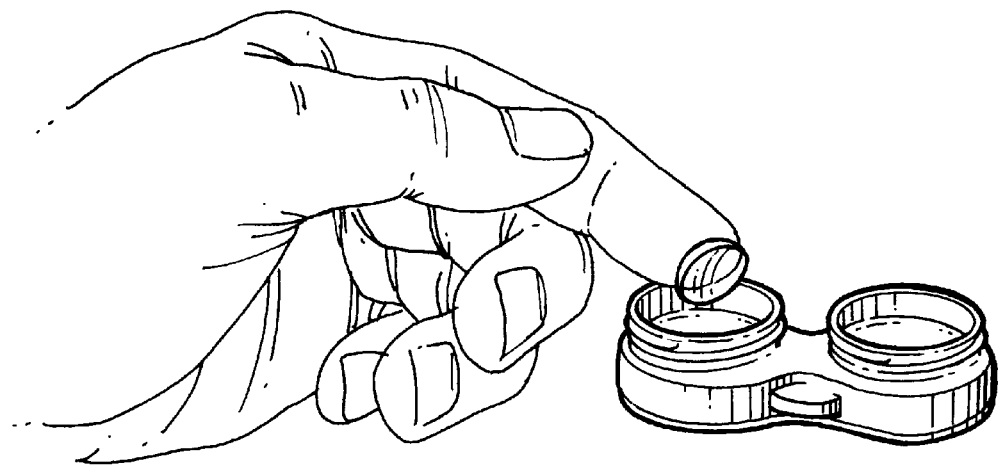
FIG. 1 illustrates a first step in accordance with the method of the invention.
Figure 2:
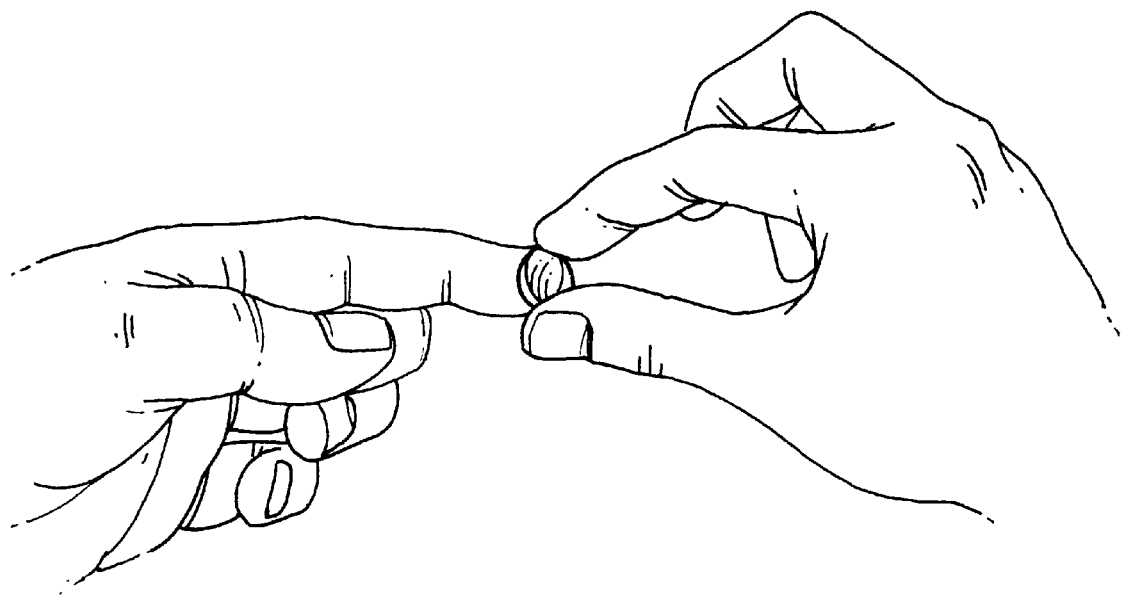
FIG. 2 illustrates a second step in accordance with the method of the invention.
Figure 3:
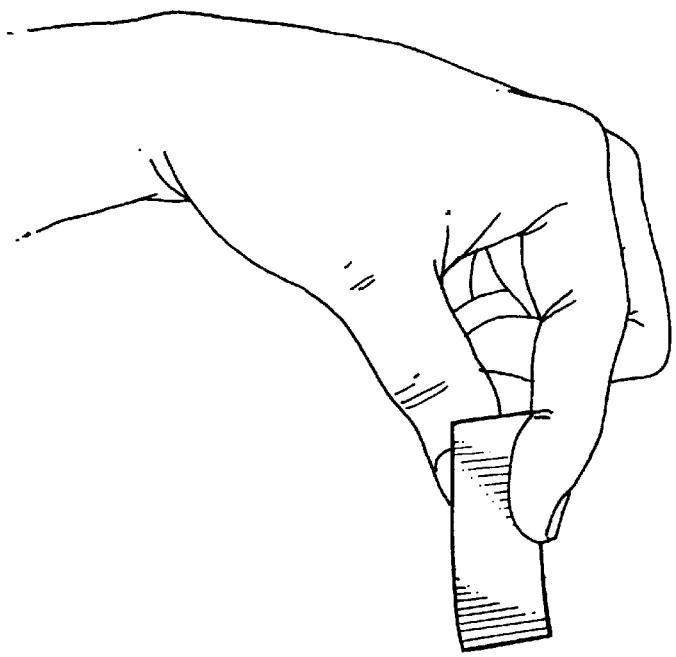
FIG. 3 illustrates a third step in accordance with the method of the invention.
Figure 4:
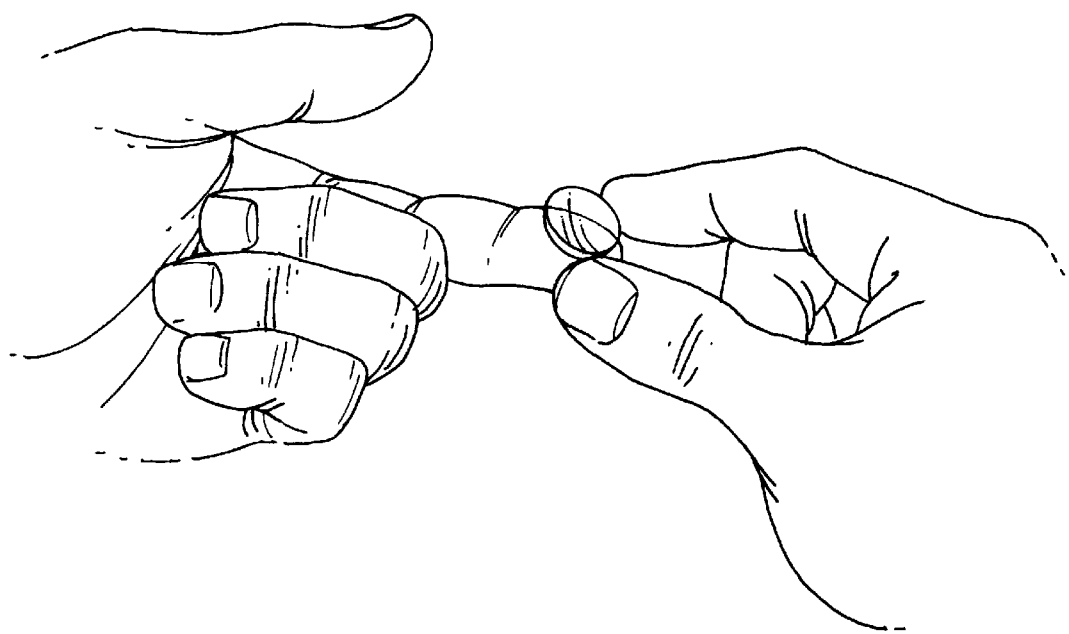
FIG. 4 illustrates a fourth step in accordance with the method of the invention.

A box of sterile, lint-free, absorbent sheets are provided to a contact lens wearer along with instructions for use to provide a system for drying the wearer's applicating finger. Referring to FIG. 1, the lens wearer is instructed to remove a contact lens from the aqueous storage solution with his applicating finger. In the next step, the lens is transferred from the applicating finger. With reference to FIG. 2, the lens is illustratively transferred to the thumb and forefinger of the opposite hand. In the step of FIG. 3, the lens wearer contacts his applicating finger, for example by a blotting or wiping motion, to one of the sterile, lint-free, absorbent paper sheets of the present system. Thereafter, referring to FIG. 4, the wearer returns the lens to his, now dry, applicating finger, ready to insert the lens onto his eye.

What is claimed is:

1. A method of processing paper to provide finger drying material used for insertion of contact lenses, the method comprising:

providing lint-free, absorbent contact lens fingertip drying paper;

cutting the paper into a plurality of sheets;

packaging the plurality of sheets into a container; and sterilizing the plurality of sheets.

2. The method of claim 1 wherein the absorbent contact lens fingertip drying paper is DD20 towelette paper.

3. The method of claim 1 wherein the sterilizing step includes applying gamma radiation to the plurality of sheets.

4. The method of claim 3 wherein the gamma radiation is applied for a period of at least eight hours.

5. A method of producing drying material, used during insertion of contact lenses, to remove contact lens storage solution from a fingertip, the method comprising:

providing lint-free paper, said paper being absorbent of the contact lens storage solution;

cutting the paper into a plurality of sheets;

packaging the plurality of sheets into a container; and sterilizing the plurality of sheets.

6. The method of claim 5 wherein the absorbent paper is towelette paper selected from the group of DD18 to DD22 towelette paper.

7. The method of claim 5 wherein each of the plurality of sheets has a square shape measuring four inches by four inches.

8. The method of claim 5 wherein the sterilizing step is performed after the packaging step.

9. The method of claim 5 wherein the sterilizing step includes applying gamma radiation to the plurality of sheets.

10. The method of claim 9 wherein the gamma radiation is applied for a period of at least eight hours.

* * * * *